United States Patent [19]
Van Handel

[11] Patent Number: 6,056,546
[45] Date of Patent: May 2, 2000

[54] CLASPLESS PARTIALS

[76] Inventor: Ambrose B. Van Handel, HC63 Box 19-A, Hammett, Id. 83627

[21] Appl. No.: 08/720,804

[22] Filed: Oct. 1, 1996

[51] Int. Cl.[7] .............................. A61C 13/02; A61C 13/28
[52] U.S. Cl. ........................ 433/169; 433/181; 433/168.1
[58] Field of Search ................................... 433/167, 172, 433/177, 178, 181, 182, 168.1, 169

[56] References Cited

U.S. PATENT DOCUMENTS

| | | | |
|---|---|---|---|
| 4,445,861 | 5/1984 | Klepacki | 433/181 |
| 4,445,862 | 5/1984 | Chiaramonte et al. | 433/181 X |
| 4,661,068 | 4/1987 | Harrison et al. | 433/181 |
| 4,744,758 | 5/1988 | Harrison et al. | 433/181 |
| 4,768,957 | 9/1988 | Segura | 433/181 |
| 5,242,304 | 9/1993 | Truax et al. | 433/181 X |

*Primary Examiner*—Nicholas D. Lucchesi

[57] ABSTRACT

Claspless removable partial dentures have a metal bar that connects to a metal framework to which is attached metal occlusal rests. The metal occlusal rests fit into prepared slots in the natural teeth on either side of the edentulous area. This metal framework supports the resilient dental material that bonds the denture teeth in their position and is bonded to the metal framework. This resilient dental material extends into the inward curve of the natural teeth on either side of the edentulous area, and by sliding into the inward curve, the partial is held in position. The metal framework is left open beneath the denture teeth so that each denture tooth can move into the resilient dental material, which then absorbs the force of mastication.

5 Claims, 2 Drawing Sheets

PRIOR ART FIG. 1
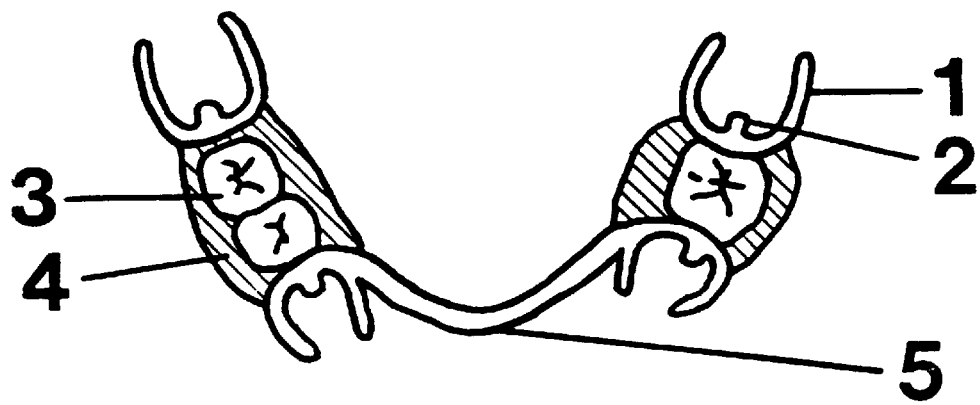
FIG. 2
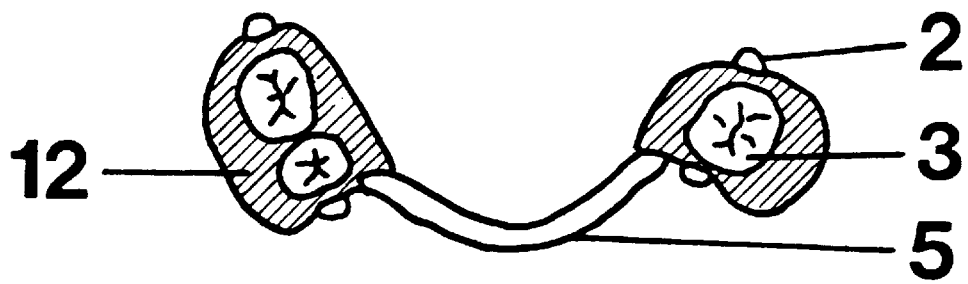
FIG. 3
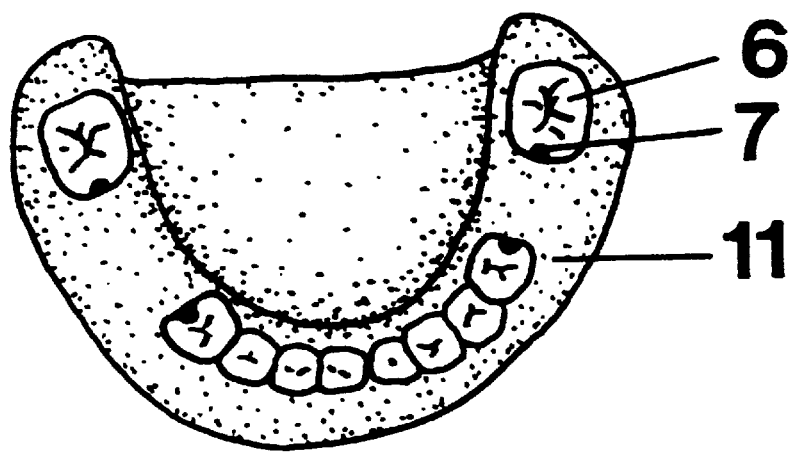

PRIOR ART FIG. 4
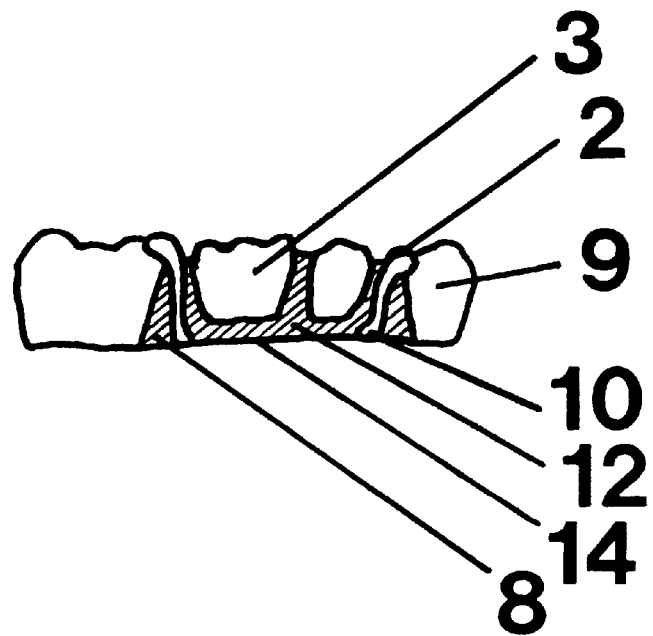
FIG. 5
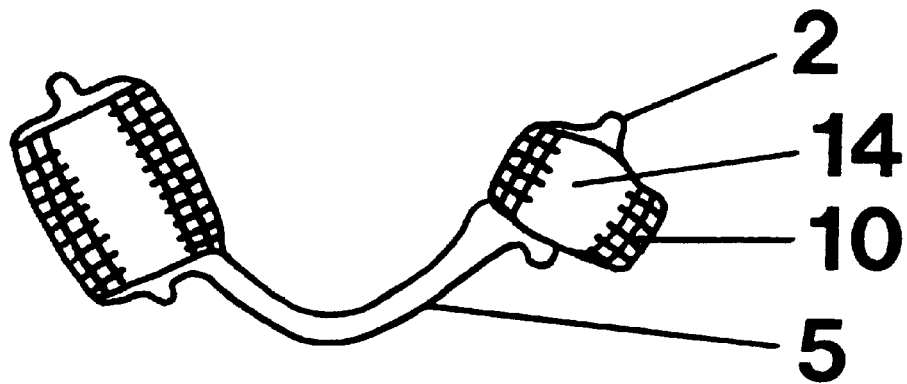

CLASPLESS PARTIALS

BACKGROUND OF THE INVENTION

1. Field of the Invention

The present invention relates to removable partial dentures which do not depend on clasps to hold them in position, but are held in place by means of resilient dental material that fits into the inward curve of the patient's natural teeth on either side of the edentulous area. This resilient dental material holds the artificial teeth in position and allows them to move into the resilient dental material, which then absorbs the shock of mastication.

2. Description of the Prior Art

Removable partial denture structures have been developed through the years to replace teeth which are missing through accident or disease. These conventional partial dentures have metal clasps which partially encircle the teeth on either side of the space where teeth are missing. These clasps often cause discomfort to the wearer and have a tendency to cause wear on the teeth to which they are partially encircling. The denture teeth are held in position by means of hard acrylic material which does not allow the denture teeth to absorb the shock of mastication.

SUMMARY OF THE INVENTION

The present invention involves a removable partial denture that does not have clasps of metal. It is held in position by the shape of the resilient dental material, which extends into the undercut caused by the inward natural curve of the patient's teeth.

This resilient dental material does not engage the entire surface of the teeth, but only about one-fourth of the tooth surface on the teeth on either side of the edentulous area.

A partial denture made according to this invention is kind to the teeth to which the partial is held in place, and is also gentle to the bone and gum tissue which it affects.

The metal framework is left open just beneath the denture teeth which allows the teeth to move into the resilient material to absorb the shock of mastication.

A metal framework supports the resilient dental material which bonds the denture teeth into position. Cast into this metal framework are metal rests which fit into the prepared notches in the natural teeth on either side of the edentulous area or areas. A lingual or palatal metal bar which does not impinge on the soft tissue beneath it, connects the metal framework.

The resilient material not only locks the partial denture teeth into position, but allows the denture teeth to move slightly into the material, from the opposing force which absorbs the shock of mastication. This shock-absorbing principle is found in our natural teeth, which are held in the bony sockets by elastic periodental membrane fibers. With our natural teeth, when the force of mastication is applied, these fibers allow the teeth to move into their bony sockets, and as soon as the pressure is relieved, the elastic periodental membrane fibers pull the teeth back into their original position. The metal occlusal rests that fit into the prepared notches in the patient's teeth prevent the metal framework and resilient material from being driven sideways or into the supporting bone and gum tissue.

The resilient material used in this invention contains an antifungal agent to prevent the growth of mold into the material, bonds to the artificial teeth and is molded to lock itself around the metal framework, and can be colored to match the patient's gum tissue.

Another advantage to this invention is that by not having clasps, food cannot become entangled in the clasps. While the partial stays in position while eating or talking, it can be removed by pushing up on the lower partial and pulling down on the upper partial to dislodge them from the inward curve of the supporting teeth.

The partials made according to this invention are made by taking an impression of the patient's dental arches and pouring a stone model. This is the conventional method. When the metal casting is made for this invention, it differs from the conventional casting in that no metal clasps are made, and the casting is left open where the denture teeth will be located. It is mounted on an articulator and the denture teeth are set in wax to occlude with the teeth of the opposing arch, as is done now. The casting and the stone model are invested in plaster in a dental flask. The wax is boiled out, and the upper and lower flasks are opened.

In the conventional case where clasps are involved, the stone model teeth that have clasps around them are cut at the gumline before the polymer and monomer of acrylic is processed in the flask; otherwise, when the upper and lower part of the flask is opened, the clasps will prevent the flask from opening or the clasps will be distorted in the process of opening.

In the present invention, where no clasps are involved, it is not advisable to cut the teeth on either side of the edentulous area.

Instead of anchoring the denture teeth in a hard acrylic as is done in the conventional method, the teeth are held in position by the resilient material. This material also holds the claspless partial in the patient's mouth when it is pressed down into the inward curve of the patient's teeth on either side of the edentulous area. By forcing the resilient material into the inward curve of the patient's natural teeth, the partial is held firmly in place without the use of metal clasps.

In this invention the palatal bar may be omitted if only one side of the dental arch is edentulous.

BRIEF DESCRIPTION OF THE DRAWINGS

FIG. 1 is a perspective view of a conventional removable partial denture with clasps.

1. metal clasps
2. metal occlusal rest
3. denture tooth
4. acrylic material
5. metal ligual bar FIG. 2 is a perspective view of a claspless removable partial denture.

2. metal occlusal rest
3. denture tooth
5. metal ligual bar
12. resilient dental material FIG. 3 is an elevated view of a stone model showing the notches for occlusal rests 6. remaining natural teeth
7. preparation made for occlusal rest
11. stone model FIG. 4 is a cross sectional view of a claspless partial denture 3. denture teeth.
2. occlusal rest
10. metal framework
14. void in metal framework 12. resilient dental material 8. inward curve of patient's tooth 9. natural tooth FIG. 5 is an elevated view of metal framework of the partial.

2. metal occlusal rest 10. metal framework 14. void in metal framework 5. lingual bar

EMBODIMENT AND METHOD OF CONSTRUCTION

FIG. 1 illustrates the present conventional partial denture. It depends upon clasps 1 to hold it into position. The rests 2 cast into the clasps 1 fit into the notches 7 cut in the natural teeth 6 shown in FIG. 3. The denture teeth 3 are held in position by the hard denture acrylic 4. The lingual bar 5 connects both sides of the partial.

FIG. 2 illustrates the dramatic change in design and construction from FIG. 1. FIG. 2 illustrates the claspless partial denture according to this invention. The occlusal rests 2 and the lingual bar 5 are connected by the underlying metal framework 10 as shown in FIG. 5. The resilient material 12 bonds the denture teeth 3 to the underlying metal framework 10.

FIG. 3 illustrates a lower stone model 11 depicting the remaining natural teeth 6 with notches 7 to accommodate the metal rests 2 of the partial.

FIG. 4 is a cross-sectional view of a claspless partial denture The casting of the metal framework 10 connects the occlusal rests 2. The resilient dental material 12 bonds the denture teeth 3 to the metal framework 10 and extends into the inward curve 8 of the patient's natural teeth 9 which locks the partial denture into position.

FIG. 5 shows the metal framework 10 of the partial in an elevated view. There is a large opening 14 cast into the metal framework 10 directly beneath where the denture teeth 3 will be located. This opening 14 allows the denture teeth 3 FIG. 4 to move into the processed resilient dental material 12 FIG. 2 to absorb the shock of mastication as pressure is applied to the denture teeth 3 FIG. 4.

By absorbing the shock of mastication it allows the denture teeth 3 FIG. 4 to move into the resilient dental material 12 FIG. 4 similar to the action of the periodental membrane fibers that hold the natural teeth 6 FIG. 3 in their bony sockets. When the pressure is relieved from the teeth 6 FIG. 3, they move back to their original position. If natural teeth are missing on only one side of the patient's arch, a partial denture can be made according to this invention without a lingual bar.

The method of construction begins with impressions of the upper and lower dental arches of the patient. The impressions are then poured up in dental stone. On these stone models, metal castings 10 are made and denture teeth 3 are waxed into position to occlude with the opposing arch. The stone models 11 together with the denture teeth 3 are waxed into position and are invested in dental plaster in dental flasks. When the plaster is set hard, the flask is placed in boiling water to remove the wax. When the upper part of the flask that contains the denture teeth 3 is removed from the lower flask that contains the metal casting 10 on the stone model 11 of the patient's dental arch, there is a void where the wax was removed. Into this void is packed the resilient dental material 12, and the upper and lower halves of the dental flask are placed in a dental clamp to hold the halves of the dental flask together while the flask and dental clamp are placed in boiling water for two hours to process the resilient dental material 12 to the denture teeth 3 and the metal framework 10.

After the resilient material has been processed, the dental clamp holding the flask is removed from the boiling water so the flask can air-cool for 15 minutes before placing it in cold water for 15 minutes. The flask is then opened and the claspless dental partial FIG. 2 is removed. Any flash of the resilient material is trimmed off with a pair of scissors. The trimmed edge of the resilient material can be smoothed by the use of a dental stone run at high speed on a dental handpiece or a laboratory motor. The resilient material can be finished by using a rag wheel and we wet pumice. The claspless partial is now complete.

I claim:

1. A removable partial denture, said denture comprising at least one denture tooth, said at least one denture tooth being held by a resilient dental material, said resilient dental material being supported by a metal framework, said metal framework comprising means for engaging prepared notches on either side of an edentulous area of a patient, wherein said resilient material engages the undercuts formed by the inward natural curve of the patient's teeth on either side of the edentulous area.

2. The removable partial denture of claim 1, said metal framework being open below the at least one denture tooth, allowing the patient's natural teeth on either side of the edentulous area to move into the resilient material, to absorb masticatory forces.

3. The removable partial denture of claim 1, wherein said means for engaging prepared notches comprises metal rests which are cast into said metal framework.

4. The removable partial denture of claim 1, wherein said resilient material further comprises an antifungal agent.

5. The removable partial denture of claim 1, wherein said resilient material is colored to match a patient's natural gum tissue color.

* * * * *